US009662200B2

United States Patent
Muchhala et al.

(10) Patent No.: US 9,662,200 B2
(45) Date of Patent: May 30, 2017

(54) INTRAOCULAR LENS DELIVERY SYSTEM WITH A DISPOSABLE PLUNGER SEGMENT AND METHOD OF USE THEREFOR

(71) Applicant: Alcon Research, Ltd., Fort Worth, TX (US)

(72) Inventors: Sushant Muchhala, Tustin, CA (US); David A. Downer, Fort Worth, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 108 days.

(21) Appl. No.: 14/475,801

(22) Filed: Sep. 3, 2014

(65) Prior Publication Data

US 2014/0371757 A1 Dec. 18, 2014

Related U.S. Application Data

(63) Continuation of application No. 12/783,144, filed on May 19, 2010, now abandoned.

(60) Provisional application No. 61/182,270, filed on May 29, 2009.

(51) Int. Cl.
*A61F 2/16* (2006.01)

(52) U.S. Cl.
CPC .......... *A61F 2/1678* (2013.01); *A61F 2/167* (2013.01)

(58) Field of Classification Search
CPC .... A61F 2/1662; A61F 2/1667; A61F 2/1672; A61F 2/1675; A61F 2/1678; A61F 2/167
USPC .......................................... 606/107; 623/6.12
See application file for complete search history.

(56) References Cited

U.S. PATENT DOCUMENTS

| | | | |
|---|---|---|---|
| 4,681,102 A | 7/1987 | Bartell | |
| 5,275,604 A | 1/1994 | Rheinish et al. | |
| 5,494,484 A | 2/1996 | Feingold | |
| 5,499,987 A | 3/1996 | Feingold | |
| 5,616,148 A | 4/1997 | Eagles et al. | |
| 5,620,450 A | 4/1997 | Eagles et al. | |
| 5,653,715 A | 8/1997 | Reich et al. | |
| 5,735,858 A | 4/1998 | Makker et al. | |
| 5,947,976 A | 9/1999 | Van Noy et al. | |
| 6,083,231 A | 7/2000 | Van Noy et al. | |
| 6,143,001 A | 11/2000 | Brown et al. | |
| 6,162,229 A | 12/2000 | Feingold et al. | |
| 6,179,843 B1 | 1/2001 | Weiler | |
| 6,334,862 B1 | 1/2002 | Vidal et al. | |
| 6,398,789 B1 | 6/2002 | Capetan | |

(Continued)

FOREIGN PATENT DOCUMENTS

BE  1 016 692    4/2007
JP  2000513955   10/2000

(Continued)

OTHER PUBLICATIONS

Corresponding PCT/US2010/035384 PCT International Search Report with mailing date Sep. 3, 2010.

(Continued)

*Primary Examiner* — Tuan V Nguyen

(57) ABSTRACT

The present invention is directed to an intraocular lens delivery system with a multi-segment plunger. More particularly, the present invention relates to an intraocular lens delivery device that includes a disposable plunger tip segment that can be attached and removed from a reusable plunger base segment.

16 Claims, 4 Drawing Sheets

(56) References Cited

U.S. PATENT DOCUMENTS

| | | |
|---|---|---|
| 2002/0151904 A1 | 10/2002 | Feingold et al. |
| 2004/0059343 A1 | 3/2004 | Shearer et al. |
| 2005/0143751 A1 | 6/2005 | Makker et al. |
| 2005/0216080 A1* | 9/2005 | Snyder ............... A61B 17/0482 623/6.47 |
| 2005/0261703 A1 | 11/2005 | Feingold et al. |
| 2006/0085013 A1 | 4/2006 | Dusek et al. |
| 2007/0265636 A1 | 11/2007 | Huynh |
| 2008/0027461 A1 | 1/2008 | Vaquero et al. |
| 2009/0292293 A1 | 11/2009 | Bogaert et al. |
| 2010/0057094 A1* | 3/2010 | Akahoshi .............. A61F 2/1662 606/107 |
| 2010/0094309 A1 | 4/2010 | Boukhny et al. |
| 2010/0152523 A1* | 6/2010 | MacDonald .......... A61M 1/122 600/16 |
| 2010/0160926 A1 | 6/2010 | Artsyukhovich et al. |

FOREIGN PATENT DOCUMENTS

| | | |
|---|---|---|
| WO | 96/15743 | 5/1996 |
| WO | 2004/091447 | 10/2004 |
| WO | 2007/005692 | 1/2007 |
| WO | 2008/014260 | 1/2008 |

OTHER PUBLICATIONS

Corresponding PCT/US2010/035384 PCT Written Opinion with mailing date Sep. 3, 2010.

\* cited by examiner

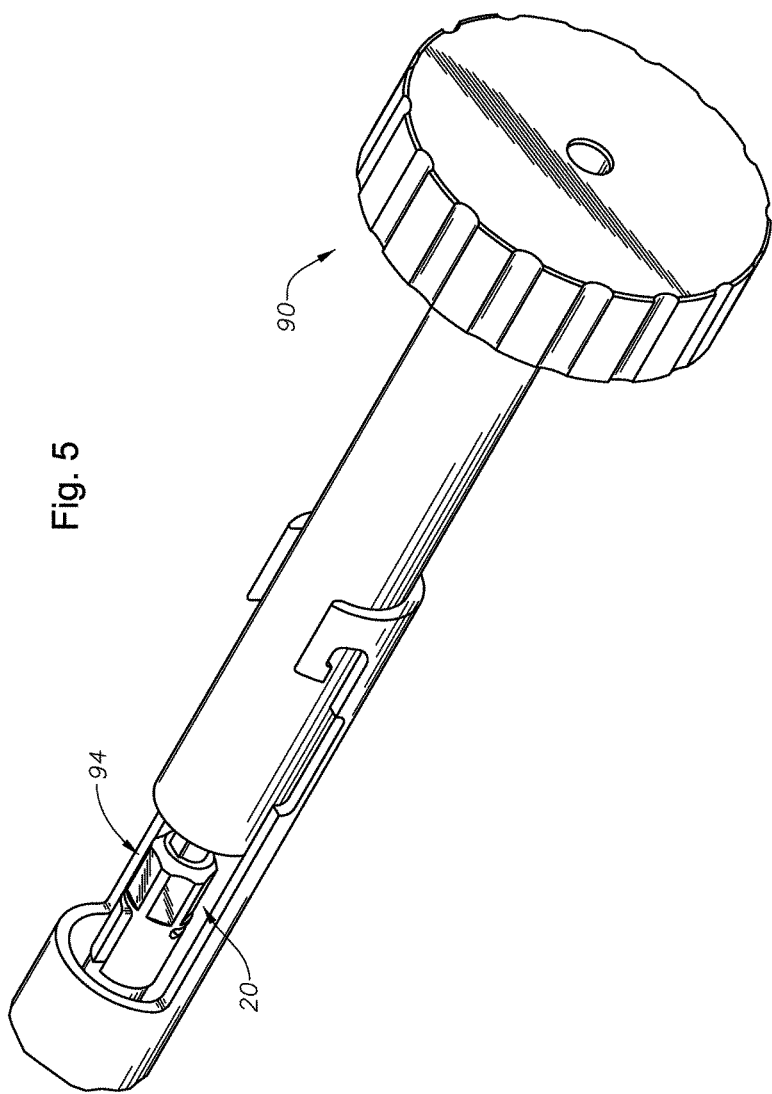

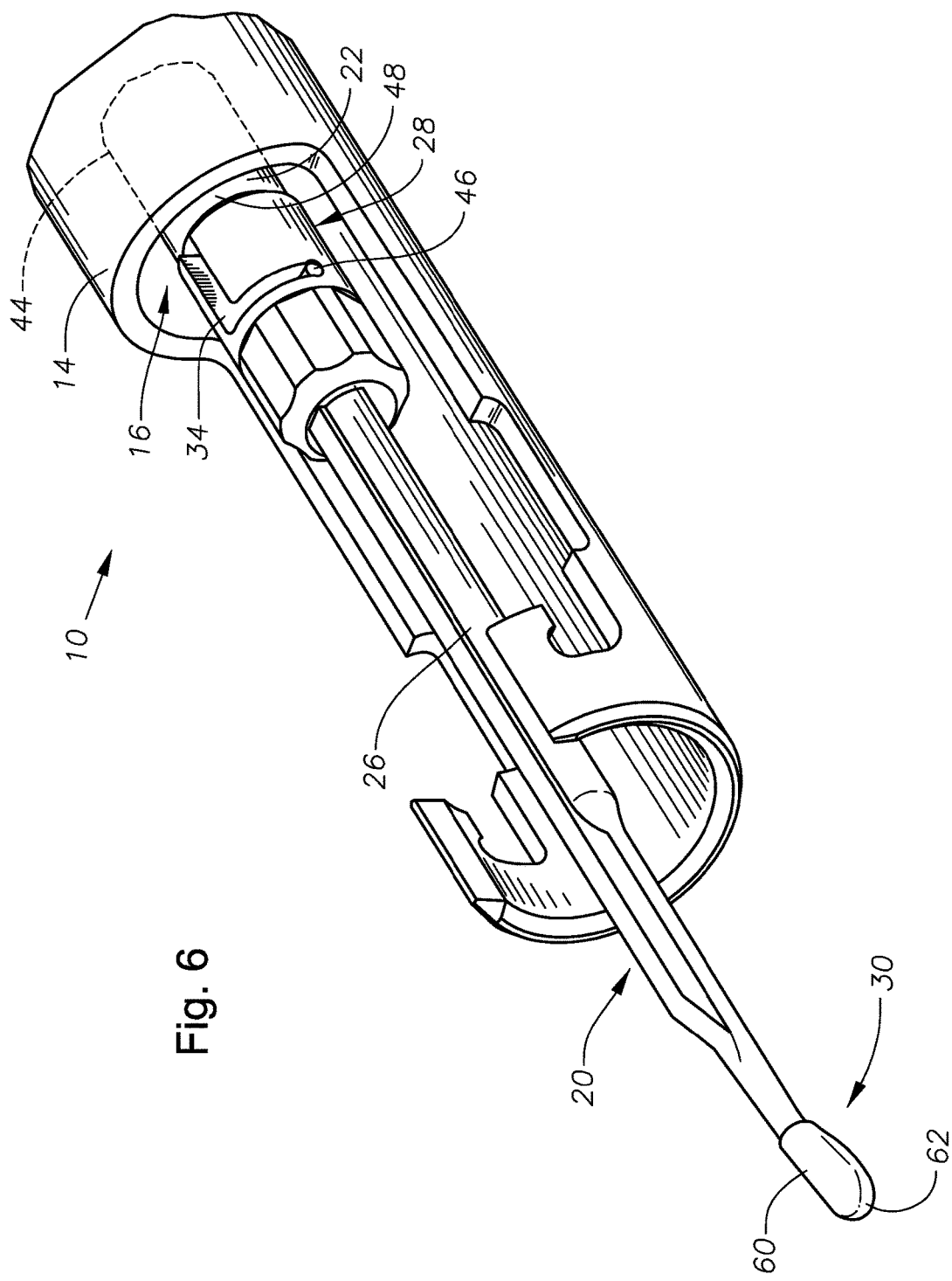

# INTRAOCULAR LENS DELIVERY SYSTEM WITH A DISPOSABLE PLUNGER SEGMENT AND METHOD OF USE THEREFOR

CROSS REFERENCE TO RELATED APPLICATION

This application is a continuation application of U.S. Utility patent application Ser. No. 12/783,144, filed May 19, 2010, now abandoned, which claims priority based on U.S. Provisional Patent Application Ser. No. 61/182,270, filed May 29, 2009, the entire contents of which are incorporated herein by reference.

TECHNICAL FIELD OF THE INVENTION

The present invention relates to an intraocular lens delivery system with a multi-segment plunger. More particularly, the present invention relates to an intraocular lens delivery system that includes a plunger comprised of a disposable plunger tip segment that can be attached and removed from a reusable plunger base segment.

BACKGROUND OF THE INVENTION

The human eye functions to provide vision by transmitting and refracting light through a clear outer portion called the cornea, and further focusing the image by way of a lens onto the retina at the back of the eye. The quality of the focused image depends on many factors including the size, shape and length of the eye, and the shape and transparency of the cornea and lens.

When trauma, age, disease or other malady cause an individual's natural crystalline lens to become less transparent, vision deteriorates because of the diminished light which can be transmitted to the retina. This deficiency in the lens of the eye is often referred to as a cataract. The treatment for this condition is surgical removal of the natural crystalline lens and implantation of an intraocular lens (IOL).

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a plunger. One commonly used injector cartridge design is illustrated in U.S. Pat. No. 4,681,102 (Bartell), and includes a split, longitudinally hinged cartridge. Other designs are illustrated in U.S. Pat. Nos. 5,494,484 and 5,499,987 (Feingold) and U.S. Pat. Nos. 5,616,148 and 5,620,450 (Eagles, et al.), the entire contents of which are incorporated herein by reference for all purposes. Still other cartridges are described in U.S. Pat. No. 5,275,604 (Rheinish, et al.), U.S. Pat. No. 5,653,715 (Reich, et al.) and U.S. Pat. No. 5,947,876 (Van Noy, et al.), the entire contents of which are incorporated herein by reference for all purposes.

The cartridge is typically preloaded with an IOL and then used as part of a delivery system to deliver the IOL to an eye of a mammal (e.g., a human). The delivery system will typically include a hand-piece that includes a plunger within a housing. The delivery cartridge is attached to the hand-piece (e.g., to the housing of the hand-piece) and then the tip of the cartridge can be inserted into an eye of a mammal. The plunger can then advance the IOL along the lumen of the cartridge and into the eye. After IOL delivery, the cartridge is typically removed from the hand-piece so that the hand-piece can be reused with a different cartridge. This system, while generally desirable, has some drawbacks.

As one exemplary drawback, the plunger of the hand-piece or the entire hand-piece must typically be sterilized (e.g., by autoclaving) after delivery of an IOL. Such sterilization is typically required because the tip of the plunger often enters the eye during insertion of the IOL and it can retain biological matter after removal from the eye. The sterilization process can require significant amounts of time and can limit the number of IOL deliveries that can be accomplished in a given time span.

As another exemplary drawback, the plunger of the hand-piece is typically sized to accommodate the size of a lumen of a particular cartridge. If it becomes desirable to use a new cartridge having a different size lumen, an entirely new plunger or entirely new hand-piece must typically be employed to accommodate that cartridge.

As yet another exemplary drawback, recent trends in IOL delivery systems have made the use of soft tip plungers quite desirable, however, the reusable plungers associated with these types of delivery system are often formed of metal or some other autoclavable material and providing such materials with a soft tip can be problematic.

It would be quite desirable to provide a plunger for an intraocular lens delivery system where that plunger overcomes one or more of the aforementioned drawbacks and/or additional drawbacks associated with conventional IOL delivery systems.

SUMMARY OF THE INVENTION

Accordingly, the present invention is directed to an improved plunger for use in IOL delivery and an IOL delivery system having such a plunger. The delivery system will typically include an elongated housing having a length and a plunger having a disposable tip segment and a reusable base segment. The reusable segment of the plunger is typically disposed within the housing and movable along the length of the housing. The reusable segment typically includes a fastening mechanism at a distal end thereof. When included, the fastening mechanism of the reusable segment is typically a projection or a cavity. The disposable segment typically includes an elongated body, a fastening mechanism at a proximate end of the elongated body and a pushing surface at a distal end of the elongated body. The fastening mechanism of the disposable segment, that that of the reusable segment is typically a projection or cavity. The projection or cavity of the fastening mechanism of the reusable segment mates with the projection or cavity of the disposable segment of the fastening mechanism of the disposable segment to releasably, but securely and rigidly, fasten the disposable segment to the reusable segment. The elongated body and fastening projection or cavity of the disposable segment are integrally molded of a single polymeric material. The single polymeric material preferably has a flexural modulus of at least 3500 MPa.

In preferred embodiment of the invention the system can include either or both of the following characteristics: an opening at a distal end of the cartridge having a maximum internal diameter that is less than 4 millimeters; and/or a soft push tip that is overmolded onto the elongated body at the distal end thereof.

BRIEF DESCRIPTION OF THE DRAWINGS

FIG. 5 is an illustration of the exemplary tool of FIG. 4 being used to manipulate the disposable plunger segment of FIGS. 1 and 2.

FIG. 6 is a perspective view of the hand-pieced of FIG. 1 wherein the plunger has been provided with an exemplary soft tip in accordance with an aspect of the present invention.

DETAILED DESCRIPTION OF THE INVENTION

The present invention is predicated upon the provision of a disposable segment for a plunger of an intraocular lens (IOL) delivery system.

Advantageously, the disposable segment of the plunger can enter the eye of a mammal during insertion of an IOL and can then be disposed of after such insertion rather than requiring sterilization. The disposable segment of the plunger is particularly desirable for use with an IOL delivery system that employs a single handpiece in conjunction with multiple cartridges. The cartridges can also be disposable such that all portions of the IOL delivery system that potentially contact the eye can be disposed of subsequent to delivery of an IOL. In such an embodiment, multiple disposable segments can, if needed or desired, be shaped or sized to correspond to the multiple different cartridges.

Figure 1:
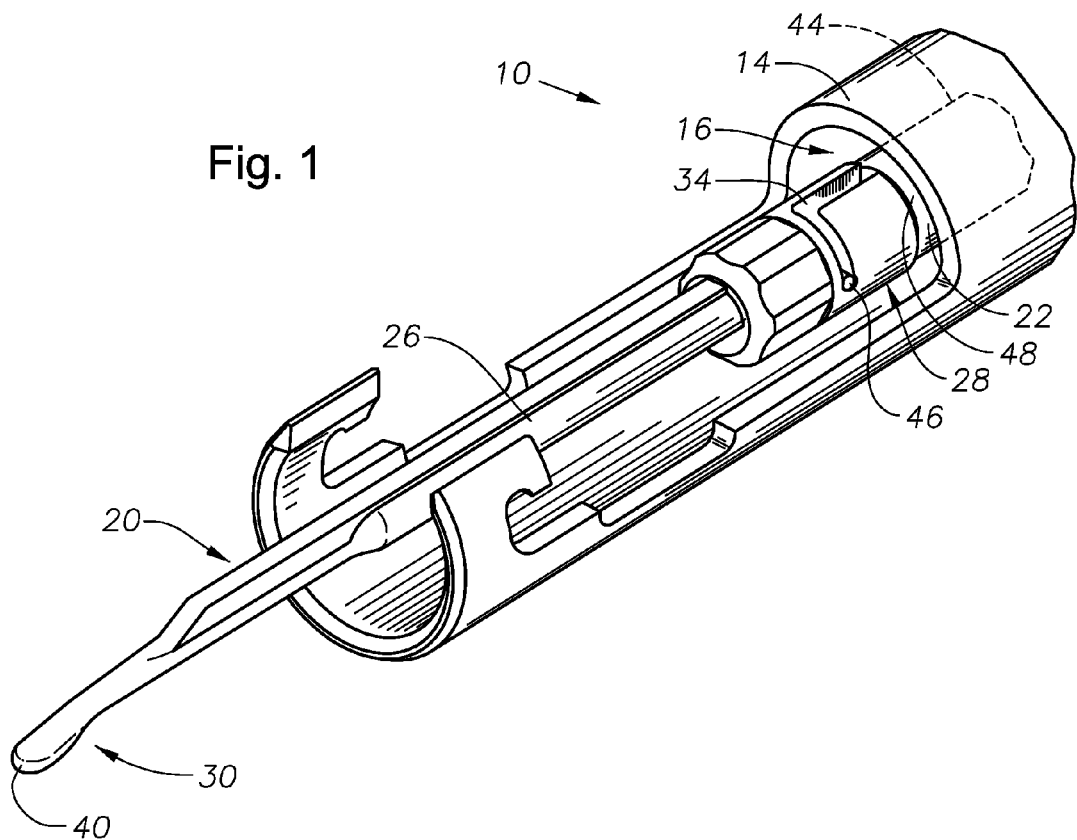
FIG. 1 is a perspective view of an exemplary hand-piece and plunger of an exemplary IOL delivery system according to an aspect of the present invention.
Figure 2:
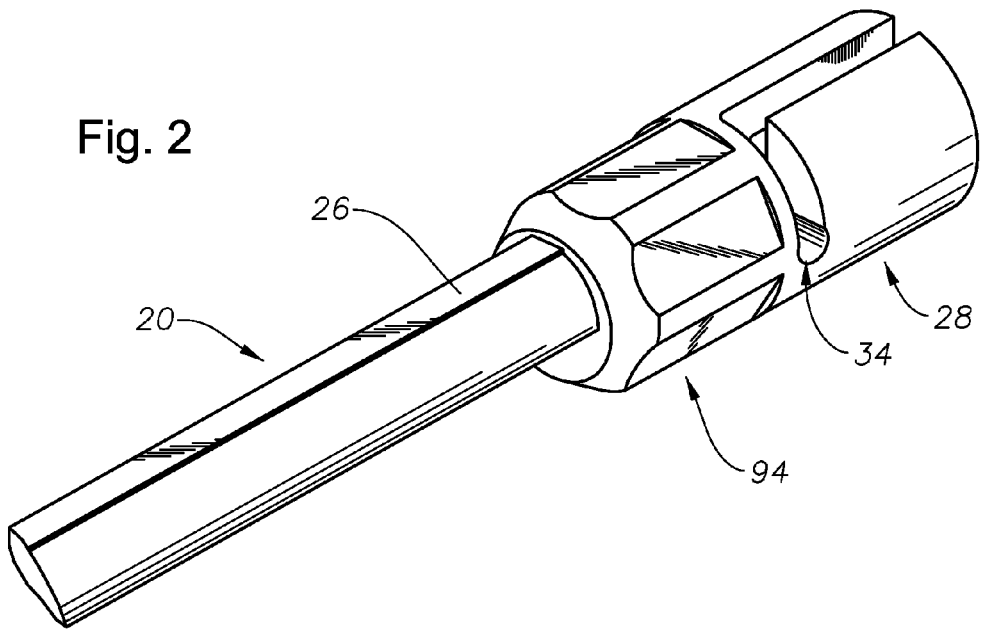
FIG. 2 is a magnified perspective view of an exemplary proximate end of an exemplary disposable plunger segment of the IOL delivery system of FIG. 1.

FIGS. 1-2 illustrate an exemplary hand-piece 10 of an exemplary IOL delivery system in accordance with the present invention. The hand-piece 10 includes a housing 14 and a plunger 16 disposed within the housing 14. The plunger 16 includes a disposable plunger tip segment 20 and a reusable plunger base segment 22.

The disposable segment 20 has an elongated body 26 with a proximate end 28 opposite a distal end 30. A fastening mechanism 34 is located at the proximate end 28 of the elongated body 26 and a pushing surface 40 is located at the distal end 30 of the elongated body 26.

The reusable segment 22 has an elongated body 44 with a fastening mechanism 46 located at a distal end 48 of the elongated body 44. In the embodiment shown, the fastening mechanism 46 of the reusable segment 22 is a projection that mates with or is received by the fastening mechanism 34 of the disposable segment 20, which is a cavity. However, it is contemplated that this system may be reversed such that the fastening mechanism of the disposable segment, which would be a projection, would mate with or be received by the fastening mechanism of the reusable segment, which would be a cavity. 34. As still another alternative, each of the fastening mechanisms could include a projection and a cavity such that the projection of each fastening mechanism mates with or is received in the cavity the other fastening mechanism.

In the embodiment illustrated, the fastening mechanisms 34, 46 cooperatively form a twist lock connector. It will be understood that various different fastening systems may be employed as long as the system releasably, but securely and rigidly, attaches the disposable segment 20 to the reusable segment 22.

The housing 14 and the reusable segment 22 of the handpiece 10 can be formed of a variety of materials and the materials for each component may be the same or different. The materials of the housing 14 and the reusable segment 22 should be durable and rigid. Such materials can include, without limitation, metals, ceramics and high strength plastics. It is generally preferable that the material[s] of the housing 14 and reusable segment 22 be easy to clean, autoclavable (i.e., have a melting temperature greater than 100° C.) or both. In a preferred embodiment, the housing 14 and the reusable segment 22 are formed of the same material and that material is a metal, most preferably stainless steel or titanium.

The disposable segment 20, including the elongated body 26 and the fastening mechanism 34 are formed of one or more molded polymeric materials, but preferably a singular integrated molded polymeric material. The pushing surface may also be formed of the molded polymeric material, however, the pushing surface may alternatively be provided by a soft tip material, which is further described herein. The molded polymeric material[s] of the disposable segment may be filled or unfilled and may include various additives such as plasticizers, tougheners, etc. The molded polymeric material is preferably injection molded or compression molded to its desired shape. In a preferred embodiment, the moldable material is a rigid plastic material, which may be a thermoset material, but is preferably a thermoplastic material. The rigid plastic material preferably exhibits one or more desirable mechanical properties. In particular, the rigid plastic material preferably has a flexural modulus of at least 3500 megapascal (MPa), more typically at least 10,000 MPa, even more typically at least 30,000 MPa and even possibly at least 50,000 MPa. Flexural modulus of these materials can be determined in accordance with ASTM D790. It is also preferable that the rigid plastic material be formed of a biologically compatible material.

Exemplary preferred rigid plastic materials for the disposable segment include, without limitation, polystyrene, acrylonitrile butadiene styrene, polycarbonate, polyamide, polyimide, polyetherimide, polyarylamide, polyetheretherketone, polybutylene terephthalate, polypropylene, polysulphone, liquid crystal polymer, combinations thereof or the like.

Advantageously, multiple disposable segments according to the present invention can be rapidly and inexpensively molded (e.g., injection molded). In turn, it becomes much more reasonable in terms of cost and other efficiencies to use a new disposable segment for each IOL insertion procedure.

As an additional advantage, these disposable segments can be more easily provided with soft tips. In particular, a relatively soft material may be overmolded or otherwise located at the distal end of the disposable segment. Preferably, the soft tip material is adhered or otherwise non-detachably attached to the material of the rest of the disposable segment. Such adhesion can be a natural adhesion between the materials (e.g., natural adhesion occurring during overmolding) or an adhesive can located between the materials. FIG. 6 illustrates such a soft tip 60, which also provides a pushing surface 62 for pushing an IOL. The soft tip material will typically exhibit an elongation at break of at least 100%, more typically at least 200% and even possibly at least 400%. The elongation at break of the soft tip material is typically no greater than 1500% and even more typically no greater than 780%. Such elongation at break can be measure in accordance with ASTM D-638. The soft tip materials will also typically have an elastic modulus of from about 100 psi to about 300 psi at an elongation of 100% and/or an elastic modulus of from about 210 psi to about 540 psi at an elongation of 300%. Such soft tips and soft tip materials are particularly desirable for pushing an IOL through a narrow lumen since the tip can deform to accommodate the lumen.

The soft tip can be formed of a variety of materials such as silicone, elastomer, combinations thereof or the like. In a preferred embodiment, the soft tip material is an elastomeric material, which may be thermoset or thermoplastic. The soft tip material should also be biologically compatible. Exemplary potential materials include, without limitation, styrenic block copolymers, polyolefin blends (TPOs), elastomeric alloys, thermoplastic polyurethanes (TPUs), thermoplastic copolyesters and thermoplastic polyamides.

Figure 3:
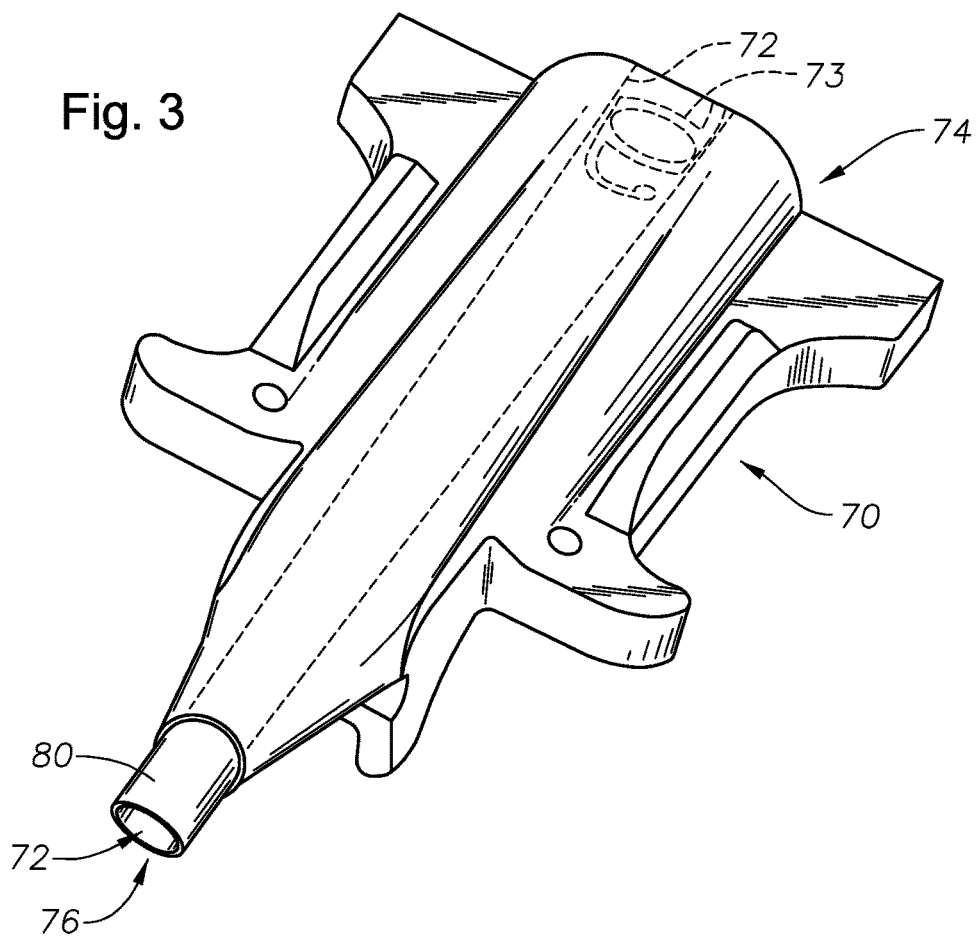
FIG. 3 is a perspective view of an exemplary pre-loaded IOL cartridge of an IOL delivery system in accordance with an aspect of the present invention.

With reference to FIG. 3, there is illustrated an exemplary cartridge 70 in accordance with the present invention. The cartridge 70 has a lumen 72 extending down its length (L) and the lumen 72 is pre-loaded with an IOL 73. The cartridge 70 and lumen 72 extend from a proximate end 74 of the cartridge 70 to a distal end 76 of the cartridge 70. The cartridge 70 includes a tip 80 at its distal end 76 and the lumen 72 extends along the tip 80. The tip 80 is defined herein to include any portion of the cartridge 70 that is inserted within an eye during insertion of an IOL within that eye. Preferably, the maximum diameter of lumen 72, taken perpendicular to the length (L), within the tip 80 is no greater than 7 millimeters (mm), more typically no greater than 5 mm and even possibly no greater than 4 mm.

The cartridge 70 may be formed of multiple different materials. In a preferred embodiment, the cartridge 70 is formed of a polymeric material and more preferably, a polypropylene material. The cartridge 70 may also be disposable. Examples of cartridges that could be used in conjunction with the present invention are described in U.S. Pat. Nos. 6,398,789, 6,143,001, 6,083,231, and 5,947,976 all of which are incorporated herein by reference for all purposes.

The plunger of the present invention is used to assist in the delivery of an IOL into an eye. The disposable segment of the plunger is releasably, but securely and rigidly, attached to the reusable segment of the plunger. Then, the plunger is advanced along the length of the housing, the cartridge or both for moving the IOL into the eye. Thereafter, the disposable segment of the plunger is removed from the reusable segment and is then preferably properly disposed of.

In the particular embodiment illustrated in FIGS. 1-5, the fastening mechanisms 34, 46 of the disposable segment 20 and the reusable segment 22 are mated or, more particularly, twist locked. The cartridge 70 is then attached to the housing 14 to align the IOL 73 with the plunger 16. The tip 80 of the cartridge 70 is then inserted into an incision in the eye. The plunger 16 is advanced along the length of the housing 14 and the length of the cartridge 70 to push the IOL 73 along the lumen 72 until it is released out of the tip 80 into the eye. The cartridge tip 80 is then removed from the incision followed by removal of the cartridge 70 from the housing 14 and removal of the disposable segment 20 from the reusable segment 22. The disposable segment 20 can then be properly disposed of.

A tool may be provided, for example as part of a kit with any combination of the handpiece, the disposable segment and the cartridge, to assist in attaching and detaching the disposable segment from the reusable segment. Preferably, such tool is formed of the same or a similar material as the disposable segment and is itself disposable. In such an embodiment, the tool can be used to assist in attaching and detaching the disposable segment from the reusable segment and can then be properly disposed of in the same fashion as the disposable segment.

Figure 4:
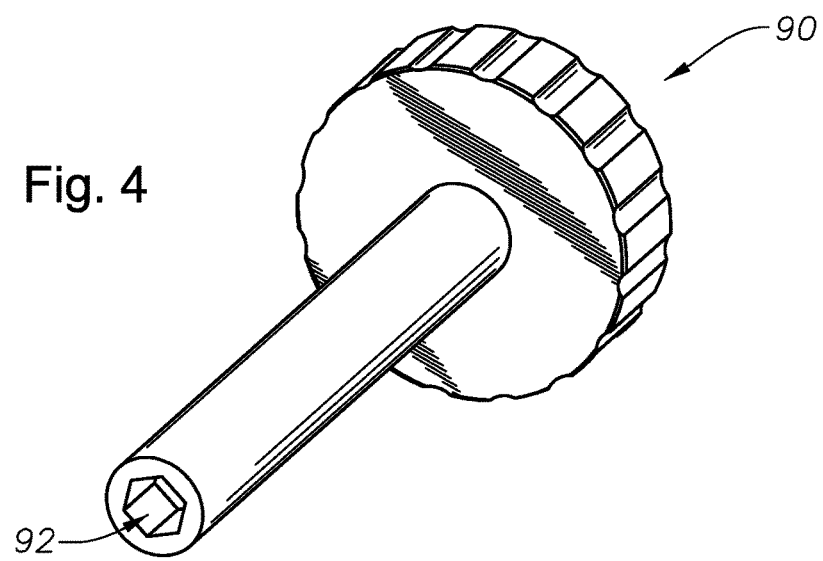
FIG. 4 is a perspective view of an exemplary tool for manipulating a disposable plunger segment in accordance with an aspect of the present invention.

With reference to FIGS. 4 and 5, an exemplary tool 90 is illustrated. As can be seen, the tool 90 includes a shaped cavity 92 (e.g., a hex shape cavity) corresponding to a hex shaped portion 94 (e.g., shown as the proximate end) of the disposable segment 20. The hex shaped portion is received in the cavity 92 and the tool 90 can then twist the disposable segment 20 to attach or detach that segment 20 from the reusable segment 22.

The plunger 16 can be advanced during IOL delivery through manual pushing of the plunger 16 or through the used of twistable threaded mechanisms. Plungers have been advanced using these techniques in products such as the MONARCH® system, which is commercially available from Alcon Laboratories, Inc., Fort Worth, Tex.

Through use of the system of the present invention, a first disposable plunger segment and, in particular embodiments, a first tool and/or a first cartridge can be used in conjunction with a hand-piece as described above for delivery of a first IOL. Then, the first disposable plunger segment, the first tool and/or the first cartridge can be replaced with a second disposable plunger, a second tool and/or a second disposable cartridge, which can be used with the same hand-piece that was used in conjunction with the first segment, tool and/or cartridge to deliver a second IOL.

Advantageously, the disposable segment of the plunger does not have to be sterilized after implantation of an IOL. Moreover, soft tips can be more effectively attached to the disposable segments for those embodiments where soft tips are desirable (e.g., in circumstances where the diameter of the cartridge opening is small). It is also contemplated that multiple different sized disposable segments may be used with a single hand-piece to deliver IOLs using cartridges having differently sized lumens. Advantageously, the segments can be specifically sized to correspond to the differently sized lumens.

The entire contents of all cited references in this disclosure are specifically incorporated herein by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. An intraocular lens delivery system, comprising:
a cartridge;
a disposable plunger tip segment comprising,
an elongated body having a proximate end and a distal end;
a fastening mechanism, which is a projection, a cavity or both, at the proximate end of the elongated body; and
a pushing surface at the distal end of the elongated body; wherein:
i. the elongated body and fastening projection or cavity are integrally molded of single polymeric material;
ii. the fastening mechanism is configured to releasably, but securely and rigidly, attach the disposable plunger tip segment to a reusable plunger segment of the intraocular lens delivery system; and
iii. the single polymeric material has a flexural modulus of at least 3500 MPa; and
a disposable tool that is used to attach the disposable plunger tip segment to the reusable plunger segment, wherein the disposable tool forms a shaped cavity that receives the proximate end of the elongated body.

2. The disposable plunger tip segment of claim 1 wherein the fastening mechanism is a cavity that lockably receives a projection extending from the reusable segment.

3. The disposable plunger tip segment of claim 2 wherein the pushing surface is provided by a soft push tip that is overmolded onto the elongated body at the distal end thereof.

4. The disposable plunger tip segment of claim 3 wherein the soft push tip is formed of a material having an elongation at break of at least 200%.

5. The disposable plunger tip segment of claim 1 wherein the single polymeric material is a thermoplastic material and has a flexural modulus of at least 30,000 MPa.

6. A kit for an intraocular delivery system that includes an elongated housing having a length and a reusable base segment of a plunger disposed within the elongated housing, the kit comprising:
a disposable tip segment of the plunger, wherein:
i. the disposable tip segment includes an elongated body, a fastening mechanism at a proximate end of the elongated body, and a pushing surface at a distal end of the elongated body;
ii. the fastening mechanism of the disposable tip segment is a projection or cavity;
iii. the projection or cavity of the disposable tip segment of the fastening mechanism mates with a projection or cavity of a fastening mechanism of the reusable segment to releasably, but securely and rigidly, fasten the disposable tip segment to the reusable segment;
iv. the elongated body and fastening projection or cavity of the disposable tip segment are integrally molded of a single polymeric material; and
v. a disposable tool that is used to attach the disposable tip segment to the reusable segment, the disposable tool comprising a shaped cavity that is configured to receive the proximate end of the elongated body, wherein upon receiving the proximate end of the elongated body, the disposable tool is operable to attach the disposable tip segment to the reusable segment.

7. The kit of claim 6 further comprising a cartridge configured to fasten to the housing wherein the cartridge comprises an opening at a distal end of the cartridge and the opening has a maximum internal diameter that is less than 4 millimeters.

8. The kit of claim 6 wherein the fastening mechanism of the disposable tip segment is a cavity that lockably receives a projection forming the fastening mechanism of the reusable segment, the projection extending from the reusable segment.

9. The kit of claim 6 wherein the pushing surface is provided by a soft push tip that is overmolded onto the elongated body of the disposable tip segment at the distal end thereof.

10. The kit of claim 9 wherein the soft push tip is formed of a material having an elongation at break of at least 200%.

11. The kit of claim 6 wherein the single polymeric material is a thermoplastic material and has a flexural modulus of at least 30,000 MPa.

12. The kit of claim 6 wherein the single polymeric material has a flexural modulus of at least 3500 MPa.

13. A kit for an intraocular lens delivery system wherein the intraocular lens delivery system includes a housing and a reusable segment, the kit comprising:
a disposable plunger tip segment comprising an elongated body having a proximate end and a distal end;
a fastening mechanism, which is a projection, a cavity or both, at the proximate end of the elongated body, the fastening mechanism is configured to releasably, but rigidly, attach the disposable plunger tip segment to the reusable segment of the intraocular lens delivery system and the fastening portion and the elongated body forming an integral component;
a pushing surface at the distal end of the elongated body; and
a disposable tool that is used to attach the disposable plunger tip segment to the reusable segment, the disposable tool comprising a shaped cavity that is configured to receive the proximate end, wherein upon receiving the proximate end, the disposable tool can twist the disposable plunger tip segment to attach the disposable plunger tip segment to the reusable segment.

14. The kit of claim 13, further comprising a disposable cartridge that is attachable or detachable from the housing.

15. The kit of claim 13, wherein the disposable plunger tip segment is formed from a material having a flexural modulus of at least 3500 MPa.

16. The kit of claim 13, wherein the pushing surface is formed from a material having an elongation at break of at least 200%.

* * * * *